US006849095B2

(12) United States Patent
Feigel et al.

(10) Patent No.: US 6,849,095 B2
(45) Date of Patent: Feb. 1, 2005

(54) AGENT AND METHOD FOR ENZYMATICALLY TANNING SKINS

(75) Inventors: Thomas Feigel, Gundersheim (DE); Manfred Palissa, Floersheim-Deisheim (DE); Ralf Pasternack, Griesheim (DE); Hans-Lothar Fuchsbauer, Muehltal (DE); Heinz-Peter Germann, Eníngen (DE); Michael Meyer, Dresden (DE)

(73) Assignee: Trumpler GmbH & Co. Chemische Fabrik, Worms (DE)

( * ) Notice: Subject to any disclaimer, the term of this patent is extended or adjusted under 35 U.S.C. 154(b) by 0 days.

(21) Appl. No.: 10/129,006

(22) PCT Filed: Jul. 3, 2001

(86) PCT No.: PCT/EP01/07586

§ 371 (c)(1),
(2), (4) Date: May 1, 2002

(87) PCT Pub. No.: WO02/18662

PCT Pub. Date: Mar. 7, 2002

(65) Prior Publication Data

US 2002/0155524 A1 Oct. 24, 2002

(51) Int. Cl.[7] ........................... C12P 21/06; C14C 3/08; C14C 11/00

(52) U.S. Cl. ............................ 8/401; 8/94.15; 8/94.21; 8/115.51; 8/401; 252/8.57; 435/193

(58) Field of Search ............................... 8/94.15, 94.21, 8/115.51, 401, 94.19; 252/8.57; 435/193

(56) References Cited

U.S. PATENT DOCUMENTS

| | | | | | |
|---|---|---|---|---|---|
| 5,531,795 | A | * | 7/1996 | Rasmussen et al. | 8/94.21 |
| 5,968,568 | A | | 10/1999 | Kuraishi et al. | |
| 6,051,033 | A | * | 4/2000 | McDevitt et al. | 8/115.51 |
| 6,140,109 | A | * | 10/2000 | McDevitt et al. | 435/263 |
| 6,200,789 | B1 | * | 3/2001 | Marmer et al. | 435/193 |

FOREIGN PATENT DOCUMENTS

| | | | |
|---|---|---|---|
| DE | 197 32 917 | | 10/1998 |
| DE | 198 14 860 | | 10/1999 |
| EP | 0 889 133 | | 1/1999 |
| WO | 93/12259 | | 6/1993 |
| WO | WO 93/12259 | * | 6/1993 |
| WO | 94/13839 | | 6/1994 |

OTHER PUBLICATIONS

Database WPI, Section Ch, Week 197629, Derwent Publications Ltd., XP002186535 & SU 487 119, Jan. 4, 1976.

* cited by examiner

*Primary Examiner*—Yogendra N. Gupta
*Assistant Examiner*—Preeti Kumar
(74) *Attorney, Agent, or Firm*—Foley & Lardner LLP

(57) ABSTRACT

Described are a composition and process for the enzymatic tanning of hides utilizing one or more transglutaminases for crosslinking the collagen in the hide.

13 Claims, No Drawings

AGENT AND METHOD FOR ENZYMATICALLY TANNING SKINS

This invention relates to a composition and process for stabilizing hides and skins by enzymatic crosslinking for the purpose of tanning, said composition and process utilizing crosslinking enzymes, especially transglutaminases.

Various forms of tanning are known for processing animal hides and skins into leather or fur. Tanning can be effected:

1. by treatment with phenolically aromatic tanning agents (vegetable or synthetic)
2. by means of covalently bonded tanning agents, for example aldehydes or isocyanates
3. using mineral tanning agents such as chromium salts or alum, aluminum sulfate or titanium or zirconium salts or
4. by means of a combination tanning system, for example chromium/vegetable, vegetable/alum, formaldehyde/vegetable or alum/chromium.

The chemistry of tanning is relatively complex. The essential factor probably resides in a crosslinking of the collagen fibers which is brought about in various ways by the various tanning agents. The tanning effect in the case of vegetable and the closely related organically synthetic compounds is due to hydrogen bonds being formed between the phenolic moieties and the peptide bonds of the collagen. When aldehydes are used for tanning, they react with free amino groups of the collagen, especially of lysine, via whose side chains the collagen peptides are crosslinked with each other. In chrome tanning, the most important tanning process, crosslinking is the result of complexation between chromium(III) salts and the carboxyl groups of the collagen.

Existing tanning processes all have advantages and disadvantages. In particular, the auxiliary materials used limit the usefulness of the waste materials of the manufacturing operation and also the usefulness of the end products when they themselves become waste at the end of their use lives.

The disadvantages of the known tanning agents include their limited availability and their minimal recoverability or reusability from leather. Wastewater treatment is costly without completely eliminating residuals in the effluent (see also Reich, Ecological aspects of important tanning processes, published in German by the association of the German leather industry, 2000).

Chrome tanning is the most widely used tanning process in the industry, for performance, economic and ecological reasons. Yet the above statements fully apply to this method of tanning as well. Even though state of the art tanneries do succeed in reducing the chromium contents of their effluents to below the stipulated maximum values, this is only possible at enormous expense. On the other hand, the quality and variety of leathers obtained by chrome tanning must be considered extremely high, so that to date no other tanning processes have been found that provide the same universality, quality and variety of styles.

It is an object of the present invention to provide a fmodern, environmentally acceptable tanning process which makes it possible to produce a high quality leather with no or at least substantially reduced amounts of chemicals.

It has now been found that this object is achieved by a composition for the enzymatic tanning of hides and skins that comprises one or more transglutaminases. The transglutaminases are used in an amount of 0.1 to 30% by weight and preferably 0.5% to 10% by weight.

It is known that transglutaminases (protein-glutamine: amine γ-glutamyltransferase EC 2.3.2.13) constitute a ubiquitous enzyme family. The enzymes catalyze the formation of stable crosslinks between proteins through the covalent linking of side chains of the amino acids glutamine and lysine (Folk and Finlayson, Adv. Protein Chem. 31, 1–133 (1977)). Transglutaminases are used in the prior art to modify food proteins in particular. The properties of the products are improved for example with regard to texture, gel strength, breaking strength, viscosity and elasticity and also taste and smell. An example of what has been described is the crosslinking of globular proteins such as casein or soy globulin, the crosslinking of muscle proteins such as actin or myosin and also the enzymatic modification of denatured proteins such as gelatin. German patent 197 32 917, moreover, describes a transglutaminase-catalyzed process for coupling proteins or peptides onto a support for immobilizing enzymes and antibodies.

As well as mammalian transglutaminases, it is especially bacterial transglutaminases which have hitherto been used for industrial processes (Zhu et al., Appl. Microbiol. Biotechnol. 44, 277–282 (1995)). A particularly suitable transglutaminase has been determined to be the bacterial transglutaminase formed from *Streptoverticillium mobaraense.* EP 0889133 and German Offenlegungsschrift 198 14 860 disclose bacterial transglutaminases, their preparation and numerous applications whereby proteinic substances are polymerized.

WO 9413839 discloses that transglutaminase can be used for finishing leather. In the process described, casein is applied to previously tanned leather and stabilized with transglutaminase. The process described there is accordingly merely a surface treatment for the purpose of modifying the applied surface layer.

In contrast, little is known to date about the enzyme-catalyzed crosslinking of the structural protein collagen. Jelenska and coworkers (Biochimica et Biophysica Acta, 616, 167–178 (1980)) report that native collagen is not a substrate of transglutaminase, meaning for the mammalian transglutaminases they used.

The previously known properties of transglutaminases in relation to the crosslinking of the side chains of protein-bound glutamine and lysine were reason to speculate whether such a crosslinking reaction might not also be possible with the native, fibrillar collagen of the hide, in which case crosslinking and hence finally also tanning of the hide could be achievable through intermolecular linking of the collagen molecules.

It has now been determined that, surprisingly, the use of transglutaminases for tanning hides offers an excellent alternative to the hitherto customary tanning processes. Treating hides with transglutaminases in a 0.1% to 30% and preferably 0.5% to about 10% aqueous solution at a pH between preferably 5 and 9 and at a temperature between 20 and 40° C. gives a crosslinked collagen matrix which exhibits famously typical leather features, namely an increased thermal stability compared with untreated collagen, leatherlike drying, the internal surface area increasing in the course of drying.

The process of the invention has the advantage that it can be carried out in the customary tanning drums present in tanneries, and no new equipment is needed for tanning with transglutaminases. A further advantage is that the tanning wastewater is completely nontoxic and presents no disposal problems, either with regard to liquid waste or with regard to solid waste, for example from thickness manipulation.

However, the tanning process of the invention can make a valuable contribution to the processes practiced in the leather industry even if it is just used for the pretanning of hides and skins. Pretanning, often a first step in the manufacture of leather or fur from hides and skins, provides the first stabilization of the collagenic tissue needed to be able to carry out any thickness leveling by splitting and/or shaving. Leveling of the pretanned hide is necessary, since it is entirely possible for the pretanned hide to differ in thickness. The hide remnants from the leveling operation have only very limited utility, if any, and are difficult to dispose of in the case of a chrome-pretannage for example. When, in contrast, the pretannage is carried out with transglutaminases, the waste hide will be in an ecologically impeccable state and can even be used as animal feed, gelatin raw material or the like. The pretanning operation can then be followed either by a further tanning process utilizing the transglutaminases or by a traditional tanning process utilizing chromium salts for example. In the latter case, an ensuing advantage would be that the total amount of chromium salts used would be appreciably reduced and hence the wastewater treatment would also be easier to carry out. In addition, the amount of chromium-contaminated waste would be reduced.

The process of the invention is useful for producing all leather varieties and furs.

What is claimed is:

1. A process for the enzymatic tanning of hides and skins, which comprises crosslinking the structural protein in the hide by the action of one or more transglutaminases.

2. A process as claimed in claim 1, wherein the hide is treated with the transglutaminase in a 0.1% to 30% aqueous solution.

3. A process as claimed in claim 1, wherein the process is effected with a pH of 2 to 11.

4. A process is as claimed in claim 1, wherein the process effected at a temperature between 4 and 60° C.

5. A process as claimed in claim 1, wherein the hide is rendered accessible to the enzyme by mechanical treatment or by addition to auxiliary materials.

6. A process as claimed in claim 1, wherein the crosslinking is augmented by the addition of suitable auxiliary materials.

7. A process as claimed in claim 1, wherein the crosslinking is effected using a thermal shock operation.

8. A process as claimed in claim 1, wherein the hide is treated with the transglutaminase in a 0.5% to 10% aqueous solution.

9. A process as claimed in claim 1, wherein the process is effected with a pH of 4 to 9.

10. A process as claimed in claim 1, wherein the process is effected at a temperature between 20 to 40° C.

11. A process as claimed in claim 5, wherein said auxiliary material is selected from the group consisting of proteases, detergents, salts and chaotropic agents.

12. A process as claimed in claim 6, wherein the auxiliary materials are selected from the group consisting of peptides, protein hydrolyzates, gelatin, polyglutamine, polyamines and polylysine.

13. A method for tanning hides or skins, which comprises contacting said hide or skin with an aqueous composition comprising one or more transglutaminases.

* * * * *